(12) United States Patent
Sato (10) Patent No.: US 11,622,678 B2
(45) Date of Patent: Apr. 11, 2023

(54) CONTROL METHOD FOR ENDOSCOPE REPROCESSOR, AND ENDOSCOPE REPROCESSOR

(71) Applicant: OLYMPUS CORPORATION, Tokyo (JP)

(72) Inventor: Norito Sato, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 516 days.

(21) Appl. No.: 16/777,960

(22) Filed: Jan. 31, 2020

(65) Prior Publication Data

US 2020/0163540 A1 May 28, 2020

Related U.S. Application Data

(63) Continuation of application No. PCT/JP2018/017813, filed on May 8, 2018.

(30) Foreign Application Priority Data

Aug. 30, 2017 (JP) .............................. JP2017-165978

(51) Int. Cl.
*A61B 1/12* (2006.01)
*A61B 1/00* (2006.01)
*A61L 2/24* (2006.01)

(52) U.S. Cl.
CPC .......... *A61B 1/125* (2013.01); *A61B 1/00006* (2013.01); *A61L 2/24* (2013.01)

(58) Field of Classification Search
None
See application file for complete search history.

(56) References Cited

U.S. PATENT DOCUMENTS 6,365,103 B1    4/2002  Fournier
2004/0118413 A1*  6/2004  Williams .................. A61L 2/18
                                                          600/101

(Continued)

FOREIGN PATENT DOCUMENTS

EP    3175775 A1    6/2017
EP    3178374 A1    6/2017

(Continued)

OTHER PUBLICATIONS

International Search Report dated Jul. 24, 2018 issued in PCT/JP2018/017813.

*Primary Examiner* — Cristi J Tate-Sims
(74) *Attorney, Agent, or Firm* — Scully, Scott, Murphy & Presser, P.C.

(57) ABSTRACT

A control method for an endoscope reprocessor is a control method for an endoscope reprocessor that includes a treatment tank, a circulation conduit that links a circulation opening and a discharge opening opened in the treatment tank to each other, a first pump that feeds liquid from the circulation opening towards the discharge opening, an atmospheric open conduit including a first end portion open to an atmosphere and a second end portion connected between the circulation opening and the first pump in the circulation conduit, a filter that filtrates a liquid flowing from the treatment tank through the circulation opening into the circulation conduit, and a sensor that detects a liquid feeding state in the circulation conduit, where the liquid feeding state in the circulation conduit is measured by the sensor during operation of the first pump in a state where the inside of the atmospheric open conduit is closed.

16 Claims, 8 Drawing Sheets

(56) References Cited

U.S. PATENT DOCUMENTS

2015/0320303 A1* 11/2015 Kawase .................... A61L 2/24
 600/117
2017/0143197 A1 5/2017 Onishi
2017/0172399 A1 6/2017 Takada

FOREIGN PATENT DOCUMENTS

| JP | 2003-521999 A | 7/2003 |
|----|---------------|--------|
| WO | WO 01/58499 A1 | 8/2001 |
| WO | WO 2015/068515 A1 | 5/2015 |
| WO | WO 2017/026138 A1 | 2/2017 |
| WO | WO 2017/033484 A1 | 3/2017 |

* cited by examiner

CONTROL METHOD FOR ENDOSCOPE REPROCESSOR, AND ENDOSCOPE REPROCESSOR

CROSS REFERENCE TO RELATED APPLICATION

This application is a continuation application of PCT/JP2018/017813 filed on May 8, 2018 and claims benefit of Japanese Application No. 2017-165978 filed in Japan on Aug. 30, 2017, the entire contents of which are incorporated herein by this reference.

BACKGROUND OF INVENTION

1. Field of the Invention

The present invention relates to a control method for an endoscope reprocessor that performs at least one type among cleaning process, disinfection process, and sterilization process to an endoscope, and also relates to an endoscope reprocessor.

2. Description of the Related Art

With regard to an endoscope used in a medical field, reprocessing such as cleaning process and disinfection process is applied to the endoscope after use. As disclosed in International Publication No. 2015/068515, for example, an endoscope reprocessing apparatus that automatically performs reprocessing on an endoscope is proposed.

The endoscope reprocessing apparatus described in International Publication No. 2015/068515 includes a cleaning disinfection tank that accommodates the endoscope, and a circulation conduit in which a liquid in the cleaning disinfection tank is sucked out from a circulation opening by a pump, and thereafter, the liquid is supplied into the cleaning disinfection tank again. In the endoscope reprocessing apparatus described in International Publication No. 2015/068515, a filter is disposed in the circulation conduit.

When clogging occurs in the filter disposed in the circulation conduit of the endoscope reprocessing apparatus, there is a possibility that a flow rate of a fluid flowing through the circulation conduit may be reduced, and the endoscope reprocessing apparatus may be unable to exhibit performance of predetermined reprocessing. In view of the above, International Publication No. 2015/068515 discloses a technology for detecting the clogging in the filter on the basis of a measured value of a flow rate sensor or a pressure sensor disposed in the circulation conduit in the endoscope reprocessing apparatus.

According to the technology disclosed in International Publication No. 2015/068515, the clogging in the filter disposed in the circulation conduit is detected on the basis of whether or not a measured value of a flow rate or a pressure in the circulation conduit at the time of running of the pump is out of a predetermined range.

SUMMARY OF THE INVENTION

According to an aspect of the present invention, there is provided a control method for an endoscope reprocessor that includes a treatment tank in which an endoscope is arranged, a circulation opening opened in the treatment tank, a discharge opening opened in the treatment tank, a circulation conduit that links the circulation opening to the discharge opening, a first pump that is arranged in the circulation conduit and feeds liquid from the circulation opening towards the discharge opening, an atmospheric open conduit including a first end portion opened in the treatment tank to be open to an atmosphere, and a second end portion connected between the circulation opening and the first pump in the circulation conduit, a second pump that is arranged in the atmospheric open conduit and feeds liquid from the second end portion towards the first end portion, a filter that is arranged in the treatment tank, the circulation opening, or between the circulation opening and a connection member to the atmospheric open conduit in the circulation conduit, and filtrates a liquid flowing from the treatment tank through the circulation opening into the circulation conduit, a sensor that is arranged between the connection member and the discharge opening in the circulation conduit, and detects a liquid feeding state in the circulation conduit, and a control device connected to the first pump, the second pump, and the sensor, the control method including measuring a first flow rate of the circulation conduit by the sensor during operation of the first pump in a state where the second pump is stopped while an inside of the atmospheric open conduit is opened, measuring a second flow rate of the circulation conduit by the sensor during operation of the first pump in a state where the inside of the atmospheric open conduit is closed, and determining presence or absence of mixture of air into the liquid flowing in the circulation conduit by comparing the measured first flow rate with the measured second flow rate.

According to an aspect of the present invention, there is provided an endoscope reprocessor including a treatment tank in which an endoscope is arranged, a circulation opening opened in the treatment tank, a discharge opening opened in the treatment tank, a circulation conduit that links the circulation opening to the discharge opening, a first pump that is arranged in the circulation conduit and feeds liquid from the circulation opening towards the discharge opening, an atmospheric open conduit including a first end portion opened in the treatment tank to be open to an atmosphere, and a second end portion connected between the circulation opening and the first pump in the circulation conduit, a second pump that is arranged in the atmospheric open conduit and feeds liquid from the second end portion towards the first end portion, a filter that is arranged in the treatment tank, the circulation opening, or between the circulation opening and a connection member to the atmospheric open conduit in the circulation conduit, and filtrates a liquid flowing from the treatment tank through the circulation opening into the circulation conduit, a sensor that is arranged between the connection member and the discharge opening in the circulation conduit, and detects a liquid feeding state in the circulation conduit, and a control device connected to the first pump, the second pump, and the sensor, in which the control device measures a first flow rate of the circulation conduit by the sensor during operation of the first pump in a state where the second pump is stopped while an inside of the atmospheric open conduit is opened, measures a second flow rate of the circulation conduit by the sensor during operation of the first pump in a state where the inside of the atmospheric open conduit is closed, and determines presence or absence of mixture of air into the liquid flowing in the circulation conduit by comparing the measured first flow rate with the measured second flow rate.

DETAILED DESCRIPTION OF THE PREFERRED EMBODIMENTS

Hereinafter, preferred embodiments of the present invention will be described with reference to the drawings. Note that a scale varies for each component in the respective drawings used in the following explanation such that respective components have sizes to an extent that the respective components can be recognized on the drawings, and the present invention is not only limited to the number of components, shapes of the components, ratio of sizes of the components, and relative positional relationships between the respective components illustrated in these drawings.

First Embodiment

Figure 1:
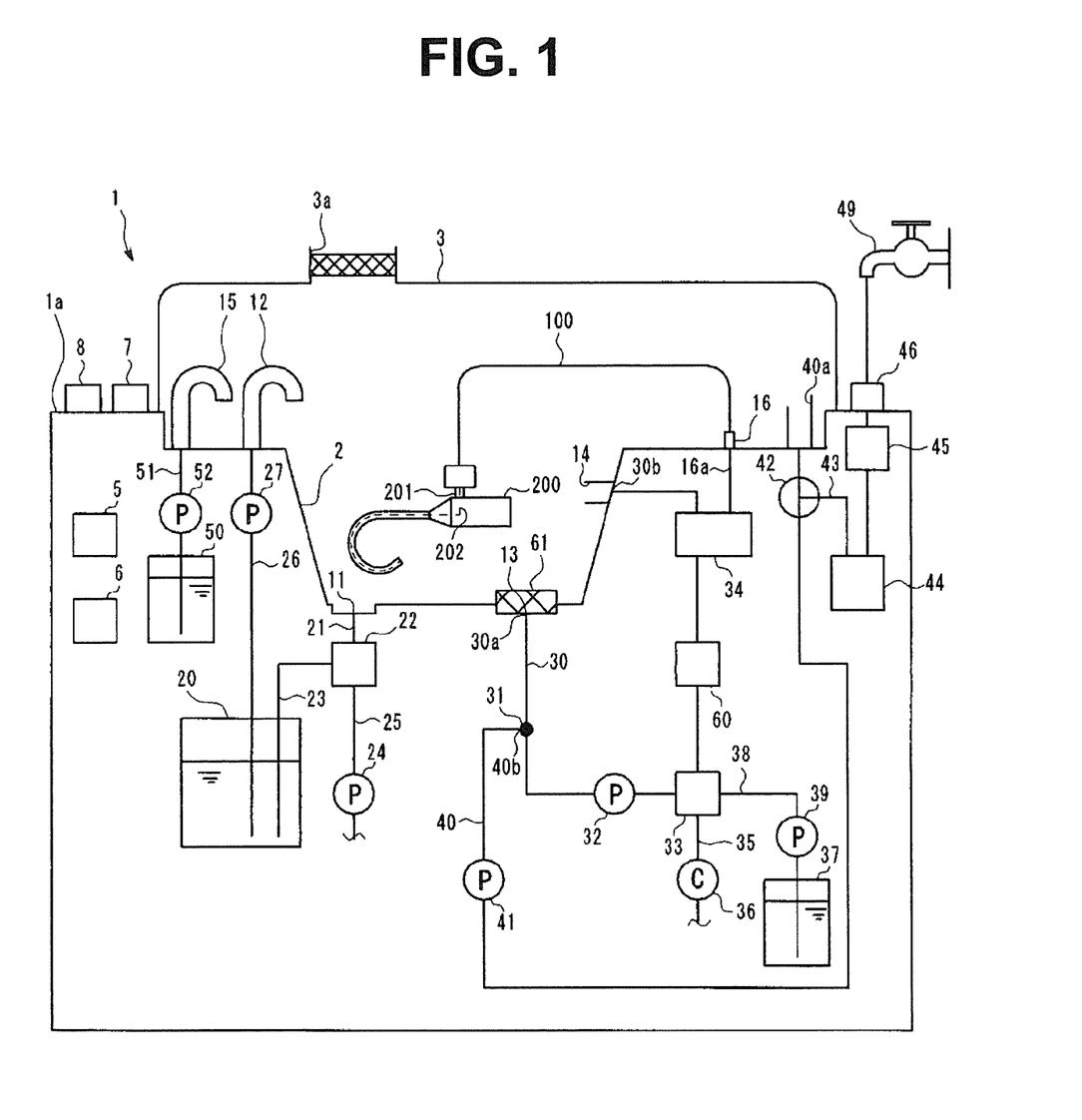
FIG. 1 is a diagram illustrating a configuration of an endoscope reprocessor according to a first embodiment.

Hereinafter, an example of embodiments of the present invention will be described. An endoscope reprocessor 1 illustrated in FIG. 1 is an apparatus that applies reprocessing to an endoscope 200. The reprocessing mentioned herein is not particularly limited and may be any one of rinsing process by water, cleaning process for removing a stain such as organic matters, disinfection process for destroying predetermined microorganisms, and sterilization process for eliminating or killing all microorganisms, or a combination of these.

Note that in the following explanation, an upper side refers to a position farther away from a ground surface with respect to a comparison target, and a lower side refers to a position closer to the ground surface with respect to the comparison target. High and low in the following explanation indicate a height relationship in a gravity direction.

The endoscope reprocessor 1 includes a control section 5 serving as a control device, a power supply section 6, a treatment tank 2, a circulation conduit 30, a first pump 32, an atmospheric open conduit 40, a sensor 60, and a filter 61.

The control section 5 can be configured by including a central processing unit (CPU), a storage device (RAM), an auxiliary storage device, an input and output device, a power control device, and the like. The control section 5 includes a configuration in which a predetermined program is executed in accordance with an instruction from a user to control operations of the respective sites constituting the endoscope reprocessor 1. The operations of the respective components included in the endoscope reprocessor 1 in the following explanation are controlled by the control section 5 unless otherwise specified.

An operation section 7 and a reporting section 8 constitute a user interface where information is exchanged between the control section 5 and the user. The operation section 7 includes an operation member that accepts an operation instruction from the user such as a push switch or a touch sensor. The operation instruction from the user is converted into an electric signal by the operation section 7 and inputted to the control section 5. The operation instruction from the user refers to a start instruction of the reprocessing, for example. Note that the operation section 7 may adopt a mode to be disposed in an electronic device separated from a main body section 1a of the endoscope reprocessor 1 which performs a wired communication or a wireless communication with the control section 5.

The reporting section 8 serving as a reporting device includes, for example, a display device that displays an image or a character, a light emitting device that emits light, a speaker that emits sound, and a vibrator that causes vibration, or a combination of these. The reporting section 8 outputs information from the control section 5 to the user. Note that the reporting section 8 may adopt a mode to be disposed in the electronic device separated from the main body section 1a of the endoscope reprocessor 1 which performs the wired communication or the wireless communication with the control section 5. In a case where the reporting section 8 adopts a mode to be disposed in the electronic device separated from the main body section 1a of the endoscope reprocessor 1, the endoscope reprocessor 1 includes a signal transmission section that transmits a signal for driving the reporting section disposed in the electronic device.

The power supply section 6 supplies power to the respective sites of the endoscope reprocessor 1. The power supply section 6 distributes the power obtained from an outside such as a commercial power supply to the respective sites. Note that the power supply section 6 may also include a power generation device or a battery.

The treatment tank 2 has a concave shape having an opening portion and can reserve a liquid therein. The endoscope 200 can be arranged inside the treatment tank 2. A configuration may also be adopted in which the plurality of endoscopes 200 can be arranged inside the treatment tank 2.

A lid 3 that opens and closes the opening portion of the treatment tank 2 is disposed in an upper part of the treatment tank 2. In a case where the reprocessing is applied to the endoscope 200 in the treatment tank 2, the opening portion of the treatment tank 2 is closed by the lid 3.

A ventilation opening 3a is disposed in the lid 3. Even in a state where the opening portion of the treatment tank 2 is closed by the lid 3, ventilation to the outside of the lid 3 can be performed via the ventilation opening 3a within the treatment tank 2. Therefore, an inside of the treatment tank 2 is in a state open to an atmosphere, and an air pressure within the treatment tank 2 is equivalent to an atmospheric pressure. Note that a filter may be disposed in the ventilation opening 3a.

A cleaning solution nozzle 15, a medicinal solution nozzle 12, a drain opening 11, a circulation opening 13, a discharge opening 14, and a first end portion 40a in the atmospheric open conduit 40 are disposed in the treatment tank 2.

The cleaning solution nozzle 15 is an opening portion communicating with a cleaning solution tank 50 that reserves a cleaning solution via a cleaning solution conduit 51. The cleaning solution is used for the cleaning process. A cleaning solution pump 52 is disposed in the cleaning solution conduit 51. The cleaning solution pump 52 is connected to the control section 5, and an operation of the cleaning solution pump 52 is controlled by the control section 5. When the cleaning solution pump 52 is operated, the cleaning solution in the cleaning solution tank 50 is transferred into the treatment tank 2.

The medicinal solution nozzle 12 is an opening portion communicating with a medicinal solution tank 20 via a medicinal solution conduit 26. The medicinal solution tank 20 reserves a medicinal solution. A type of the medicinal solution reserved in the medicinal solution tank 20 is not particularly limited, but according to the present embodiment, in one example, the medicinal solution is a disinfection solution used for the disinfection process or a sterilization solution used for the sterilization process. A peracetic acid aqueous solution is exemplified as the disinfection solution or the sterilization liquid.

A medicinal solution pump 27 is disposed in the medicinal solution conduit 26. When the medicinal solution pump 27 is operated, the medicinal solution in the medicinal solution tank 20 is transferred into the treatment tank 2 via the medicinal solution conduit 26 and the medicinal solution nozzle 12.

According to the present embodiment, in one example, the medicinal solution can be used again in a case where the medicinal solution keeps a medicinal efficacy even after the reprocessing. Thus, the endoscope reprocessor 1 includes a configuration in which the medicinal solution in the treatment tank 2 is collected to be returned into the medicinal solution tank 20. The configuration in which the medicinal solution in the treatment tank 2 is collected to be returned into the medicinal solution tank 20 will be described below.

The drain opening 11 is an opening portion disposed in a lowest location in the treatment tank 2. The drain opening 11 is connected to a discharge conduit 21. The discharge conduit 21 communicatively connects the drain opening 11 and a switching valve 22. A collection conduit 23 and a disposal conduit 25 are connected to the switching valve 22. The switching valve 22 can be switched to a state where the discharge conduit 21 is closed, a state where the discharge conduit 21 communicates with the collection conduit 23, or a state where the discharge conduit 21 communicates with the disposal conduit 25. The switching valve 22 is connected to the control section 5, and an operation of the switching valve 22 is controlled by the control section 5.

The collection conduit 23 communicatively connects the medicinal solution tank 20 and the switching valve 22. The disposal conduit 25 communicatively connects a drain facility that accepts the liquid discharged from the endoscope reprocessor 1 and the switching valve 22. A discharge pump 24 is disposed in the disposal conduit 25. The discharge pump 24 is connected to the control section 5, and an operation of the discharge pump 24 is controlled by the control section 5.

When the switching valve 22 is set in a closed state, the liquid can be reserved in the treatment tank 2. When the medicinal solution is reserved in the treatment tank 2, in a case where the switching valve 22 is set in a state where the discharge conduit 21 communicates with the collection conduit 23, the medicinal solution is transferred from the treatment tank 2 to the medicinal solution tank 20.

When the switching valve 22 is set in a state where the discharge conduit 21 communicates with the disposal conduit 25 to operate the discharge pump 24, the liquid in the treatment tank 2 is delivered to the drain facility via the disposal conduit 25.

The circulation opening 13 and the discharge opening 14 are opening portions opened in the treatment tank 2. The circulation opening 13 is disposed in a vicinity of a bottom surface of the treatment tank 2. A position of the discharge opening 14 is not particularly limited as long as the position is in the treatment tank 2.

A first end portion 30a in the circulation conduit 30 is connected to the circulation opening 13. A second end portion 30b in the circulation conduit 30 is connected to the discharge opening 14. In other words, the circulation conduit 30 links the circulation opening 13 to the discharge opening 14.

A connection portion 31 serving as a connection member, the first pump 32, a channel block 33, a switching valve unit 34, and the sensor 60 are arranged in the circulation conduit 30.

The connection portion 31 is arranged in a midway position in the circulation conduit 30, and the atmospheric open conduit 40 that will be described below is connected to the connection portion 31.

The first pump 32 is arranged between the connection portion 31 and the discharge opening 14 in the circulation conduit 30. In other words, the connection portion 31 is arranged between the circulation opening 13 and the first pump 32 in the circulation conduit 30.

The first pump 32 is driven to feed the liquid in the circulation conduit 30 from the circulation opening 13 towards the discharge opening 14. The first pump 32 is connected to the control section 5, and an operation of the first pump 32 is controlled by the control section 5.

The channel block 33 is arranged between the first pump 32 and the discharge opening 14 in the circulation conduit 30. A first check valve that allows a flow of the liquid in the circulation conduit 30 only in a direction from the circulation opening 13 towards the discharge opening 14 is disposed in the channel block 33.

An air intake conduit 35 and an alcohol conduit 38 are connected to the channel block 33. The air intake conduit 35 and the alcohol conduit 38 are connected in a segment between the first check valve and the discharge opening 14 in the circulation conduit 30 in the channel block 33. A second check valve and a third check valve that allow flows of a fluid in directions respectively from the air intake conduit 35 and the alcohol conduit 38 only towards the inside of the circulation conduit 30 are disposed in the channel block 33.

In other words, the fluid does not flow from the inside of the circulation conduit 30 towards insides of the air intake conduit 35 and the alcohol conduit 38 by the second check valve and the third check valve. The fluid that flows from the insides of the air intake conduit 35 and the alcohol conduit 38 into the circulation conduit 30 flows in the direction from the channel block 33 towards the discharge opening 14 inside the circulation conduit 30 by the first check valve.

One end portion of the air intake conduit 35 is connected to the channel block 33 as described above, and the other end portion is opened to the atmosphere. Note that although not illustrated in the drawing, a filter that filtrates a passing gas is disposed in the other end portion of the air intake conduit 35. An air compressor 36 is disposed in the air intake conduit 35 and is driven to transfer the gas in the air intake conduit 35 towards the channel block 33.

The alcohol conduit 38 communicatively connects an alcohol tank 37 that reserves alcohol and the channel block 33. For example, ethanol is exemplified as the alcohol reserved in the alcohol tank 37. An alcohol concentration can be appropriately selected. An alcohol pump 39 is disposed in the alcohol conduit 38 and is driven to transfer the alcohol in the alcohol tank 37 towards the channel block 33.

The air compressor 36 and the alcohol pump 39 are connected to the control section 5, and these operations are controlled by the control section 5. When the operation of the air compressor 36 is started, the air is fed to the circulation conduit 30. When the operation of the alcohol pump 39 is started, the alcohol in the alcohol tank 37 is fed to the circulation conduit 30.

The switching valve unit 34 is arranged between the channel block 33 and the discharge opening 14 in the circulation conduit 30. The switching valve unit 34 includes a first valve that opens and closes the circulation conduit 30.

An endoscope connection conduit 16a is connected to the switching valve unit 34. The switching valve unit 34 includes a second valve that opens and closes the endoscope connection conduit 16a. In a case where the second valve is in an opened state, the circulation conduit 30 communicates with the endoscope connection conduit 16a. The switching valve unit 34 is connected to the control section 5, and an operation of the switching valve unit 34 is controlled by the control section 5.

The endoscope connection conduit 16a connects the switching valve unit 34 to an endoscope connection portion 16. The endoscope connection portion 16 is arranged in the treatment tank 2. The endoscope connection portion 16 is connected to a pipe sleeve 202 disposed in the endoscope 200 via an endoscope connection tube 100. Note that a configuration may be adopted in which the endoscope connection portion 16 is directly connected to the pipe sleeve 202 without an intermediation of the endoscope connection tube 100.

When the operation of the first pump 32 is started while the first valve that opens and closes the circulation conduit 30 in the switching valve unit 34 is set in an opened state and the second valve that opens and closes the endoscope connection conduit 16a is set in a closed state in a case where the liquid is reserved in the treatment tank 2, the liquid in the treatment tank 2 flows out from the discharge opening 14 into the treatment tank 2 through the circulation opening 13 and the circulation conduit 30.

When the operation of the first pump 32 is started while the first valve that opens and closes the circulation conduit 30 in the switching valve unit 34 is set in a closed state and the second valve that opens and closes the endoscope connection conduit 16a is set in an opened state in a case where the liquid is reserved in the treatment tank 2, the liquid in the treatment tank 2 flows into a conduit of the endoscope 200 through the circulation opening 13, the circulation conduit 30, the endoscope connection conduit 16a, and the endoscope connection portion 16.

In the atmospheric open conduit 40, the first end portion 40a is opened to the atmosphere, and a second end portion 40b is connected to the connection portion 31 in the circulation conduit 30. The first end portion 40a is arranged above a highest water level of the liquid reserved in the treatment tank 2. A position of the first end portion 40a is not particularly limited, but according to the present embodiment, in one example, the first end portion 40a is arranged in the treatment tank 2. As described above, the inside of the treatment tank 2 is in an atmospheric open state even in a state where the lid 3 is closed.

A second pump 41 and a three-way valve 42 are arranged in the atmospheric open conduit 40. The second pump 41 is driven to feed the liquid in the atmospheric open conduit 40 from the connection portion 31 towards the first end portion 40a. The second pump 41 is connected to the control section 5, and an operation of the second pump 41 is controlled by the control section 5.

The second pump 41 according to the present embodiment does not include a check function, and the flow of the fluid is allowed from the first end portion 40a in the atmospheric open conduit 40 towards the connection portion 31 when the second pump 41 stops.

The three-way valve 42 is arranged between the second pump 41 and the first end portion 40a in the atmospheric open conduit 40. A water supply conduit 43 is connected to the three-way valve 42. The three-way valve 42 can perform switching to a state where the first end portion 40a communicates with the connection portion 31 or a state where the first end portion 40a in the atmospheric open conduit 40 communicates with the water supply conduit 43 after the atmospheric open conduit 40 is set in an opened state.

The water supply conduit 43 communicatively connects the three-way valve 42 and a water supply source connection portion 46. A water introduction valve 45 that opens and closes the water supply conduit 43 and a water filter 44 that filtrates water are disposed in the water supply conduit 43. The water filtrated by the water filter 44 is set in a sterile state. The water supply source connection portion 46 is connected to a water supply source 49 such as a water system that feeds water via a hose or the like.

The three-way valve 42 and the water introduction valve 45 are connected to the control section 5, and these operations are controlled by the control section 5.

In a case where the liquid is reserved in the treatment tank 2, when the three-way valve 42 is set in a state where the first end portion 40a in the atmospheric open conduit 40 and the connection portion 31 communicate with each other to start the operation of the second pump 41, the liquid in the treatment tank 2 flows into the atmospheric open conduit 40 through the circulation opening 13, the circulation conduit 30, and the connection portion 31, and the liquid flows out from the first end portion 40a into the treatment tank 2.

When the three-way valve 42 is set in a state where a circulation nozzle communicates with the water supply conduit 43 to set the water introduction valve 45 in an opened state, the water supplied from the water supply source 49 flows out from the first end portion 40a into the treatment tank 2.

Note that in the atmospheric open conduit 40, a flow resistance from the first end portion 40a to the connection portion 31 is preferable higher than a flow resistance from the circulation opening 13 in the circulation conduit 30 to the connection portion 31 in a case where the three-way valve 42 is set in a state where the first end portion 40a in the atmospheric open conduit 40 communicates with the connection portion 31.

The sensor 60 detects a liquid feeding state of the circulation conduit 30. In more detail, the sensor 60 detects the presence or absence of mixture of the air in the liquid flowing in the circulation conduit 30 in a case where the treatment tank 2 reserves the liquid and the first pump 32 is driven. The air mixed in the liquid flowing in the circulation conduit 30 refers to air flowing into the circulation conduit 30 through the atmospheric open conduit 40 in which the first end portion 40a is opened to the atmosphere.

In FIG. 1, in one example, the sensor 60 is arranged in a segment between the channel block 33 and the switching valve unit 34 in the circulation conduit 30, but the sensor 60 may also be arranged in a segment between the connection portion 31 and the first pump 32 in the circulation conduit 30, or may also be arranged in a segment between the first pump 32 and the channel block 33 in the circulation conduit 30.

The sensor 60 may be, for example, an air sensor that directly detects the presence or absence of the mixture of the air in the liquid flowing in the circulation conduit 30 or may also adopt a mode in which, for example, a pressure, a flow rate, or a flow velocity in the circulation conduit 30 is measured, and the presence or absence of the mixture of the air in the liquid flowing in the circulation conduit 30 is determined on the basis of the measurement result. For example, the sensor 60 may also adopt a mode in which the presence or absence of the flowing of the air in a direction from the first end portion 40a towards the connection portion 31 the atmospheric open conduit 40 is detected. A configuration may also be adopted in which the presence or absence of the mixture of the air in the liquid flowing in the circulation conduit 30 is determined by the control section 5 on the basis of the output from the sensor 60.

According to the present embodiment, in one example, the sensor 60 is a flow rate sensor that is arranged between the connection portion 31 and the discharge opening 14 in the circulation conduit 30 and detects a flow rate of the fluid flowing in the circulation conduit 30. According to the present embodiment, the control section 5 determines the presence or absence of the mixture of the air in the liquid flowing in the circulation conduit 30 on the basis of the measurement result of the flow rate by the sensor 60.

The filter 61 is arranged in one location or a plurality of locations in the treatment tank 2, in the circulation opening 13, and between the circulation opening 13 and the connection portion 31 in the circulation conduit 30, and filtrates the liquid flowing from the inside of the treatment tank 2 through the circulation opening 13 into the circulation conduit 30. In FIG. 1, in one example, the filter 61 is arranged so as to cover the circulation opening 13.

Next, filter clogging detection process executed by the control section 5 in the endoscope reprocessor 1 including the above-mentioned components will be described.

Figure 2:
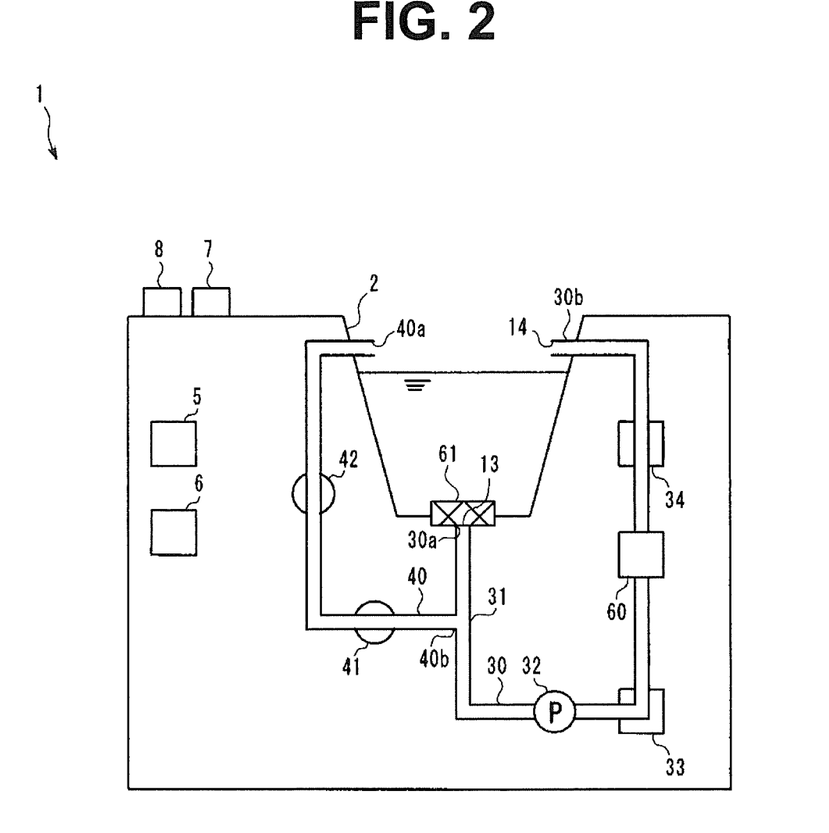
FIG. 2 is a diagram illustrating a configuration related to filter clogging detection process in the endoscope reprocessor according to the first embodiment.
Figure 3:
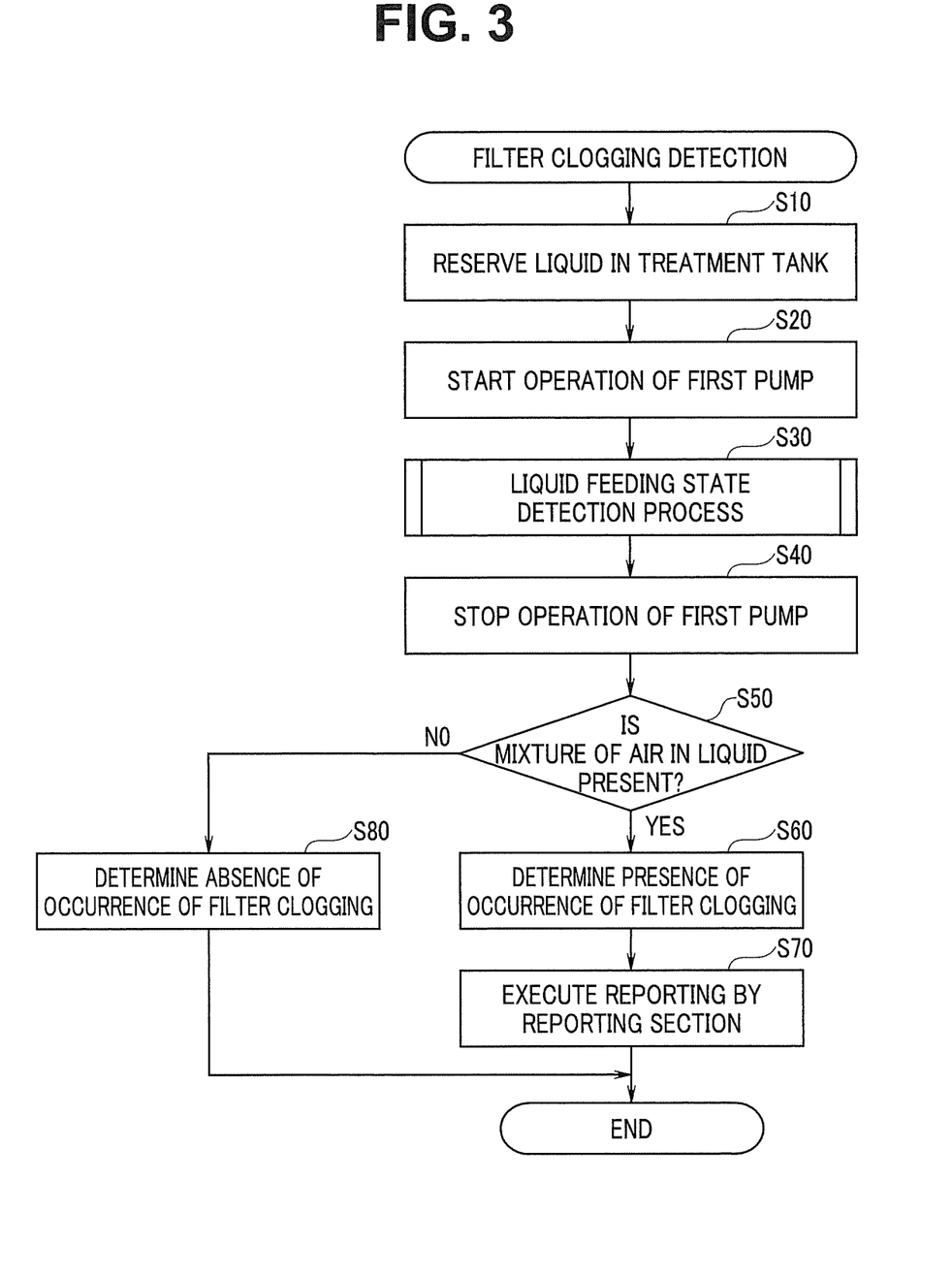
FIG. 3 is a flowchart of the filter clogging detection process according to the first embodiment.

FIG. 2 is a drawing illustrating only main components related to the filter clogging detection process of the endoscope reprocessor 1. FIG. 3 is a flowchart of the filter clogging detection process.

In the filter clogging detection process, first, in step S10, the control section 5 reserves a predetermined amount of liquid in the treatment tank 2. The liquid reserved in the treatment tank 2 in step S10 is not particularly limited, and is the water supplied from the water supply source 49, the medicinal solution reserved in the medicinal solution tank 20, or a mixed solution of the water and the cleaning solution reserved in the cleaning solution tank 50. Note that the liquid reserved in the treatment tank 2 in step S10 may be used as it is for the reprocessing as which is performed following the filter clogging detection process.

In a case where the filter clogging detection process is executed after the reprocessing, the liquid reserved in the treatment tank 2 in the reprocessing performed immediately before may be used as it is. In this case, in step S10 can be omitted.

The amount of the liquid reserved in the treatment tank 2 in step S10 is an amount at which the filter 61 and the circulation opening 13 are regularly below a liquid level of the liquid in a case where the first pump 32 is driven. Therefore, after the liquid is reserved in the treatment tank 2 in step S10, even when the first pump 32 is driven, air is not sucked into the circulation conduit 30 from the circulation opening 13.

Next, in step S20, the control section 5 starts the operation of the first pump 32. In step S20, the second pump 41 is set in the stopped state. In step S20, the control section 5 sets the first valve that opens and closes the circulation conduit 30 in the switching valve unit 34 in an opened state, and sets the second valve that opens and closes the endoscope connection conduit 16a in a closed state. As a result of the running of the first pump 32, the liquid in the treatment tank 2 flows from the discharge opening 14 through the circulation opening 13 and the circulation conduit 30 to return into the treatment tank 2.

Next, in step S30, the control section 5 executes liquid feeding state detection process in the circulation conduit 30 using the sensor 60. As described above, according to the present embodiment, the sensor 60 is the flow rate sensor that measures the flow rate of the liquid flowing in the circulation conduit 30.

Figure 4:
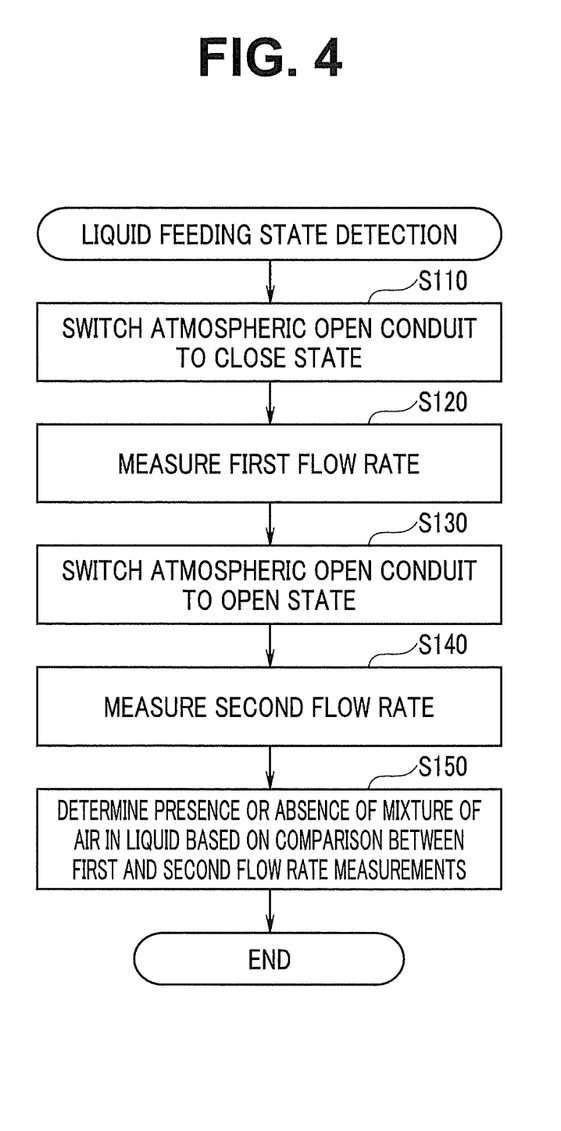
FIG. 4 is a flowchart of liquid feeding state detection process according to the first embodiment.

FIG. 4 is a flowchart of the liquid feeding state detection process performed by the control section 5 in step S30. As described above, during the execution of the liquid feeding state detection process, the first pump 32 is in a running state, and the second pump 41 is in a stopped state.

As illustrated in FIG. 4, in the liquid feeding state detection process, first, in step S110, the control section 5 switches the three-way valve 42 to a state where the atmospheric open conduit 40 is closed. As a result of the execution in step S110, the first end portion 40a in the atmospheric open conduit 40 and the connection portion 31 in the circulation conduit 30 are in a cut-off state from each other.

Next, in step S120, the control section 5 measures a first flow rate Q1 corresponding to a flow rate in the circulation conduit 30 in a state where the atmospheric open conduit 40 is closed on the basis of the output of the sensor 60. In other words, the first flow rate Q1 is the flow rate in the circulation conduit 30 in a state where the connection portion 31 is not opened to the atmosphere via the atmospheric open conduit 40.

Note that according to the present embodiment, the control section 5 sets an average value of measurement results by the sensor 60 during a predetermined period T1 as the first flow rate Q1. According to the present embodiment, the control section 5 measures a first fluctuation index R1 indicating a fluctuation in the flow rate during the predetermined period T1. The first fluctuation index R1 may be a fluctuation band corresponding to a difference between a highest value and a lowest value of the flow rate during the predetermined period T1 or may be a standard deviation of the measurement results of the flow rate during the predetermined period T1. According to the present embodiment, in one example, the first fluctuation index R1 is the fluctuation band corresponding to the difference between the highest value and the lowest value of the flow rate during the predetermined period T1.

Next, in step S130, the control section 5 switches the three-way valve 42 to a state where the atmospheric open conduit 40 is set in an opened state, and the first end portion 40a communicates with the connection portion 31. As a result of the execution in step S130, the connection portion 31 in the circulation conduit 30 is set in a state open to the atmosphere via the atmospheric open conduit 40.

Next, in step S140, the control section 5 measures a second flow rate Q2 corresponding to a flow rate in the circulation conduit 30 in a state where the atmospheric open conduit 40 is opened on the basis of the output of the sensor 60.

According to the present embodiment, the control section 5 sets an average value of measurement results by the sensor 60 during the predetermined period T1 as the second flow rate Q2. The control section 5 measures a second fluctuation index R2 indicating a fluctuation in the flow rate during the predetermined period T1. The second fluctuation index R2 may be a fluctuation band corresponding to the difference between the highest value and the lowest value of the flow rate during the predetermined period T1 or may be a standard deviation of the measurement results of the flow rate during the predetermined period T1. According to the present embodiment, in one example, the second fluctuation index R2 is the fluctuation band corresponding to the difference between the highest value and the lowest value of the flow rate during the predetermined period T1.

Next, in step S150, the control section 5 determines the presence or absence of the mixture of the air in the liquid flowing in the circulation conduit 30 on the basis of a comparison between the measurement result by the sensor 60 in step S120 and the measurement result by the sensor 60 in step S140. According to the present embodiment, the measurement result by the sensor 60 in step S120 includes the first flow rate Q1 and the first fluctuation index R1, and the measurement result by the sensor 60 in step S140 includes the second flow rate Q2 and the second fluctuation index R2.

As described above, the air mixed in the liquid flowing in the circulation conduit 30 refers to the air flowing into the circulation conduit 30 through the atmospheric open conduit 40 in which the first end portion 40a is opened to the atmosphere. Therefore, the measurement result (the first flow rate Q1 and the first fluctuation index R1) by the sensor 60 in step S120 in a state where the atmospheric open conduit 40 is closed is based on a state where the air is not mixed in the liquid flowing in the circulation conduit 30 for certain. On the other hand, the measurement result (the second flow rate Q2 and the second fluctuation index R2) by the sensor 60 in step S140 in a state where the atmospheric open conduit 40 is opened is based on a state where there is a possibility that the air may be mixed in the liquid flowing in the circulation conduit 30.

Hereinafter, the clogging in the filter 61 refers to a state where the flow resistance when the liquid passes thought the inside of the filter 61 exceeds a predetermined value.

For example, in a case where the clogging in the filter 61 that filtrates the liquid flowing from the treatment tank 2 through the circulation opening 13 into the circulation conduit 30 does not occur, at the time of the running of the first pump 32, even when the atmospheric open conduit 40 is in an opened state, since the flow resistance of the filter 61 is low, the air is not sucked into the circulation conduit 30 through the atmospheric open conduit 40.

Therefore, in a case where the clogging in the filter 61 does not occur, the measurement result (the first flow rate Q1 and the first fluctuation index R1) by the sensor 60 in step S120 in a state where the atmospheric open conduit 40 is closed and the measurement result (the second flow rate Q2 and the second fluctuation index R2) by the sensor 60 in step S140 in a state where the atmospheric open conduit 40 is opened become substantially the same results.

For example, in a case where the clogging in the filter 61 occurs, when the atmospheric open conduit 40 is opened at the time of the running of the first pump 32, since the flow resistance of the filter 61 is high, the air is sucked into the circulation conduit 30 through the atmospheric open conduit 40.

Therefore, in a case where the clogging in the filter 61 does not occur, the measurement result (the first flow rate Q1 and the first fluctuation index R1) by the sensor 60 in step S120 in a state where the atmospheric open conduit 40 is closed and the measurement result (the second flow rate Q2 and the second fluctuation index R2) by the sensor 60 in step S140 in a state where the atmospheric open conduit 40 is opened become different results.

More specifically, when the clogging in the filter 61 occurs and the air is mixed in the liquid in the circulation conduit 30, the flow rate of the liquid flowing in the circulation conduit 30 is decreased, and also the fluctuation in the flow rate is increased. In other words, when the clogging in the filter 61 occurs and the air is mixed in the liquid in the circulation conduit 30, the second flow rate Q2 becomes lower than the first flow rate Q1, and the second fluctuation index R2 becomes higher than the first fluctuation index R1.

In view of the above, according to the present embodiment, in step S150, in a case where a ratio of the second flow rate Q2 to the first flow rate Q1 is lower than or equal to a predetermined value, and also the ratio of the second fluctuation index R2 to the first fluctuation index R1 is higher than or equal to a predetermined value, the control section 5 determines that the air is mixed in the liquid flowing in the circulation conduit 30.

Note that in step S150, the control section 5 may also determine that the air is mixed in the liquid flowing in the circulation conduit 30 in a case where the ratio of the second fluctuation index R2 to the first fluctuation index R1 is higher than or equal to the predetermined value without taking the first flow rate Q1 and the second flow rate Q2 into account.

In step S150, the control section 5 may also determine that the air is mixed in the liquid flowing in the circulation conduit 30 in a case where the ratio of the second flow rate Q2 to the first flow rate Q1 is lower than or equal to the predetermined value without taking the first fluctuation index R1 and the second fluctuation index R2 into account.

After the execution in step S150, the control section 5 ends the liquid feeding state detection process, and proceeds to step S40 in FIG. 3. In step S40, the control section 5 stops the operation of the first pump 32.

Next, as illustrated in step S50, the control section 5 proceeds to step S60 in a case where it is determined that the air is mixed in the liquid flowing in the circulation conduit 30 in the liquid feeding state detection process, and otherwise, proceeds to step S80.

In step S60, the control section 5 determines that the clogging in the filter 61 occurs. In step S70, the control section 5 drives the reporting section 8 and notifies the user of the occurrence of the clogging in the filter 61. On the other hand, in step S80, the control section 5 determines that the clogging in the filter 61 does not occur. Thus, the filter clogging detection process by the control section 5 is ended.

Note that in a case where the reporting section 8 adopts a mode to be disposed in the electronic device separated from the main body section 1a of the endoscope reprocessor 1, in step S70, the control section 5 transmits a signal for driving the reporting section 8 disposed in the electronic device to the electronic device.

As described above, in the filter clogging detection process executed by the endoscope reprocessor 1 according to the present embodiment, the presence or absence of the mixture of the air from the atmospheric open conduit 40 in the liquid flowing in the circulation conduit 30 at the time of the running of the first pump 32 is detected, and the presence or absence of the occurrence of the clogging in the filter 61 is determined on the basis of the presence or absence of the mixture of the air.

According to the present embodiment, since the presence or absence of the mixture of the air in the liquid flowing in the circulation conduit 30 is not determined by using an absolute value of the flow rate or pressure in the circulation conduit 30 as a reference, the detection is not affected by an individual difference of the performance of the first pump 32 or aging of the pump performance.

Therefore, in accordance with the endoscope reprocessor 1 according to the present embodiment and the control method for the endoscope reprocessor 1, the clogging occurrence in the filter 61 can be automatically accurately detected.

Note that according to the present embodiment, the sensor 60 is the flow rate sensor that measures the flow rate of the liquid in the circulation conduit 30, but the sensor 60 may also be a pressure sensor that measures a pressure in the circulation conduit 30. Since an inner diameter of the circulation conduit 30 in the location where the sensor 60 is arranged is a known value, the control section 5 can calculate the flow rate of the liquid in the circulation conduit 30 on the basis of the measured value of the pressure in the circulation conduit 30. Therefore, according to the present embodiment, even when the sensor 60 is set as the pressure sensor, the control section 5 can detect the presence or absence of the mixture of the air from the atmospheric open conduit 40 in the liquid flowing in the circulation conduit 30 at the time of the running of the first pump 32 on the basis of the measurement result by the sensor 60.

Second Embodiment

Hereinafter, a second embodiment of the present invention will be described. Only differences from the first embodiment will be described below. Components similar to the components of the first embodiment are assigned with the same reference signs, and descriptions of those components are accordingly omitted.

Figure 5:
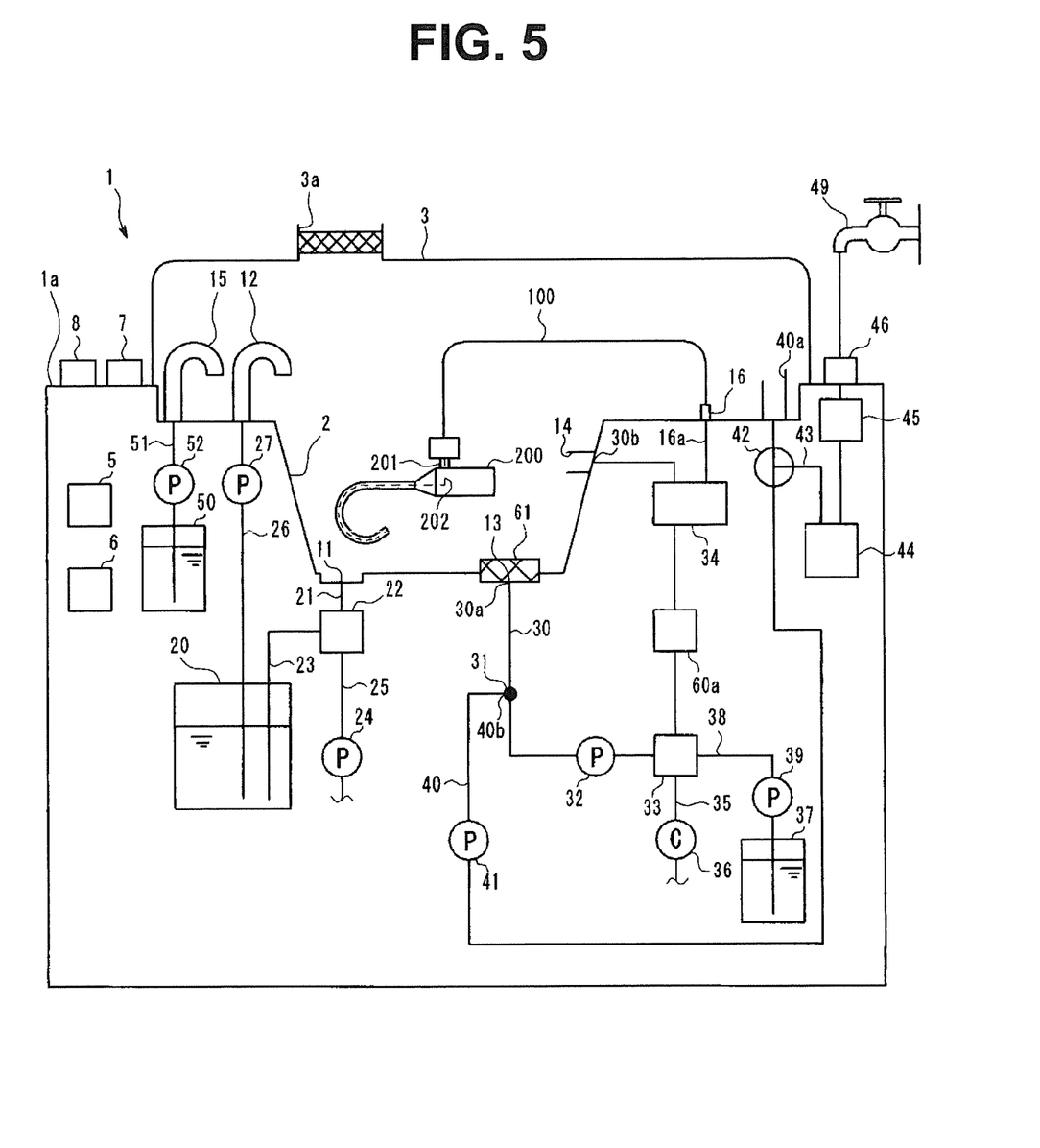
FIG. 5 is a diagram illustrating a configuration of an endoscope reprocessor according to a second embodiment.

The endoscope reprocessor 1 according to the present embodiment illustrated in FIG. 5 is different from the first embodiment in that a sensor 60a is an air sensor that directly detects the presence or absence of the mixture of the air in the liquid flowing in the circulation conduit 30.

Figure 6:
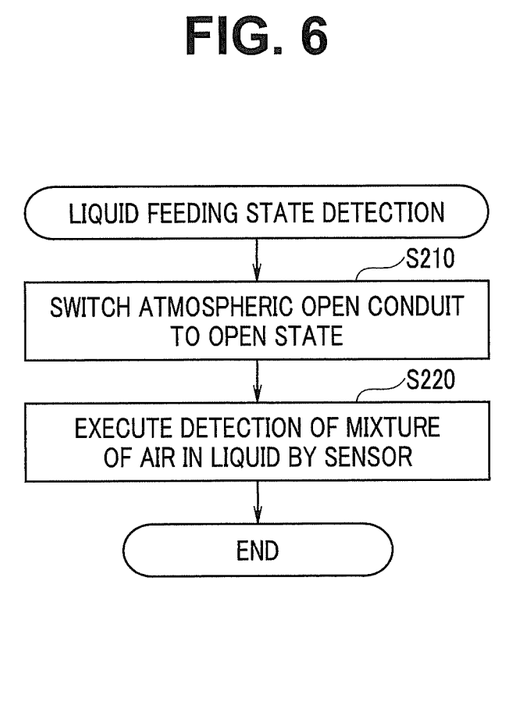
FIG. 6 is a flowchart of the liquid feeding state detection process according to the second embodiment.

FIG. 6 is a flowchart of the liquid feeding state detection process performed by the control section 5 according to the present embodiment. In the liquid feeding state detection process, first, in step S210, the control section 5 switches the three-way valve 42 to a state where the atmospheric open conduit 40 is set in an opened state, and the first end portion 40a communicates with the connection portion 31. As a result of the execution in step S210, the connection portion 31 in the circulation conduit 30 is set in a state open to the atmosphere via the atmospheric open conduit 40. In step S220, the control section 5 executes the presence or absence of the mixture of the air in the liquid by the detection of the sensor 60. Thus, the liquid feeding state detection process according to the present embodiment is ended.

Similarly as in the first embodiment, in the filter clogging detection process executed by the endoscope reprocessor 1 according to the present embodiment, the presence or absence of the mixture of the air from the atmospheric open conduit 40 in the liquid flowing in the circulation conduit 30 at the time of the running of the first pump 32 is detected, and the presence or absence of the occurrence of the clogging in the filter 61 is determined on the basis of the presence or absence of the mixture of the air.

According to the present embodiment, since the presence or absence of the mixture of the air in the liquid flowing in the circulation conduit 30 is not detected by using the absolute value of the flow rate or the pressure in the circulation conduit 30 as the reference, the detection is not affected by the individual difference of the performance of the first pump 32 or the aging of the pump performance.

Therefore, in accordance with the endoscope reprocessor 1 according to the present embodiment and the control method for the endoscope reprocessor 1, the clogging occurrence in the filter 61 can be automatically accurately detected.

Third Embodiment

Hereinafter, a third embodiment of the present invention will be described. Only differences from the first embodiment will be described below. Components similar to the components of the first embodiment are assigned with the same reference signs, and descriptions of those components are accordingly omitted.

Figure 7:
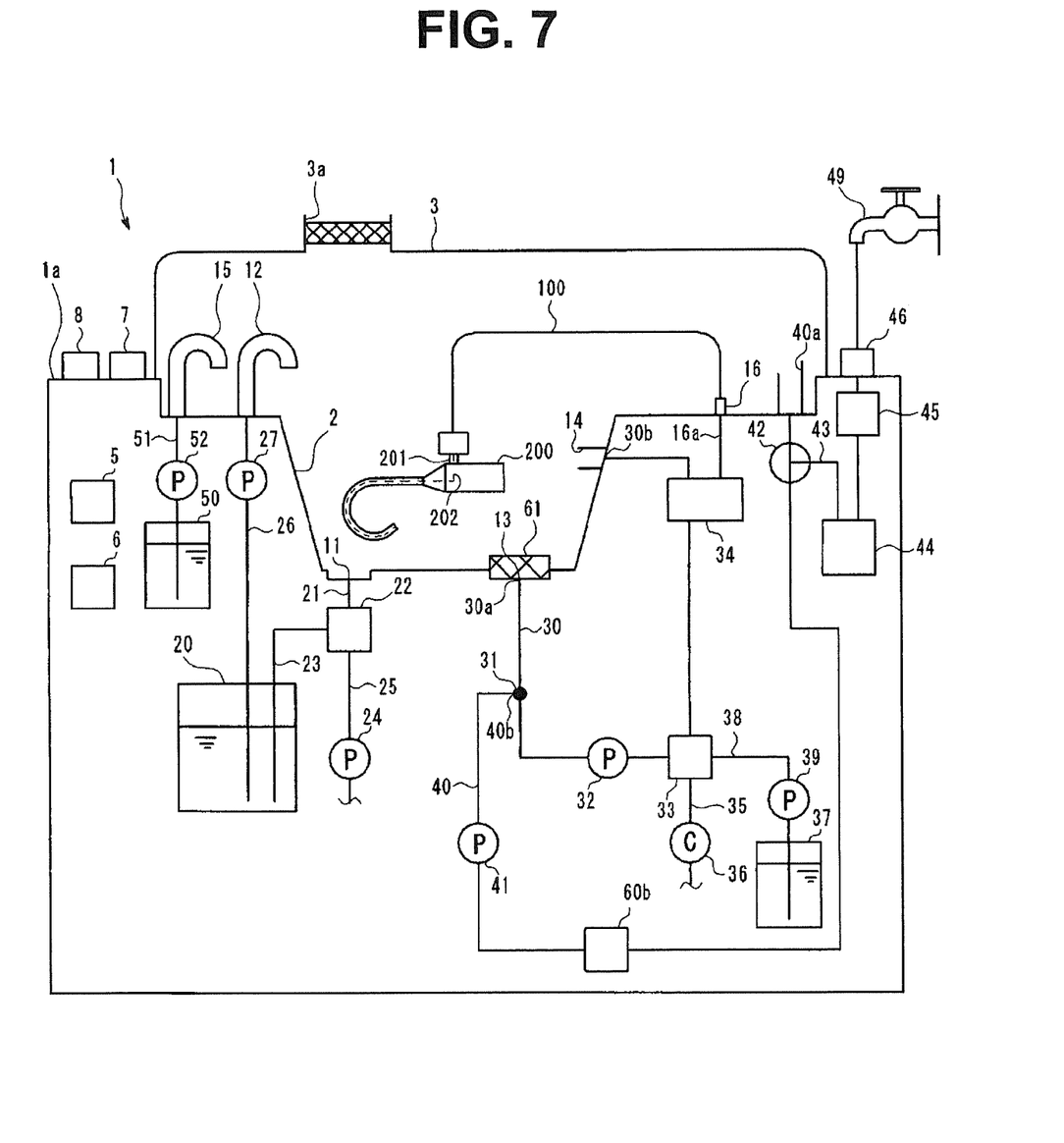
FIG. 7 is a diagram illustrating a configuration of an endoscope reprocessor according to a third embodiment.

The endoscope reprocessor 1 according to the present embodiment illustrated in FIG. 7 is different from the first embodiment in that a sensor 60b is arranged in the atmospheric open conduit 40, and the sensor 60b is a wind direction and wind velocity sensor that detects a flow velocity and a flow direction of the air in the atmospheric open conduit 40.

Figure 8:
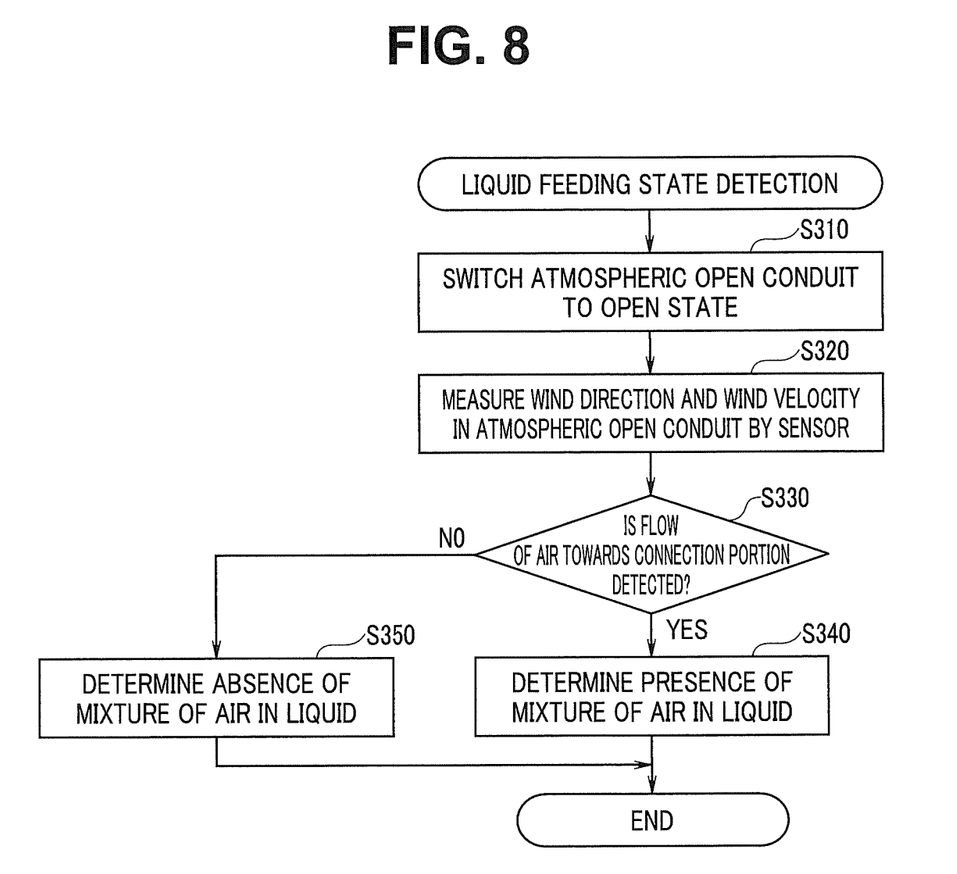
FIG. 8 is a flowchart of the liquid feeding state detection process according to the third embodiment.

FIG. 8 is a flowchart of the liquid feeding state detection process performed by the control section 5 according to the present embodiment. In the liquid feeding state detection process, first, in step S310, the control section 5 switches the three-way valve 42 to a state where the atmospheric open conduit 40 is set in an opened state, and the first end portion 40a communicates with the connection portion 31. As a result of the execution in step S310, the connection portion 31 in the circulation conduit 30 is set in a state open to the atmosphere via the atmospheric open conduit 40. Next, in step S320, the control section 5 executes the measurement of the flow velocity and the flow direction of the air in the atmospheric open conduit 40 by the sensor 60.

Next, in step S330, the control section 5 determines whether or not the flow of the air at a predetermined flow velocity or higher in a direction from the first end portion 40a towards the connection portion 31 is generated at the predetermined flow velocity or higher in the atmospheric open conduit 40. In step S330, in a case where it is determined that the flow of the air at the predetermined flow velocity or higher in the direction from the first end portion 40a towards the connection portion 31 is generated, the control section 5 proceeds to step S340, and determines that the mixture of the air in the liquid flowing in the circulation conduit 30 occurs.

In step S330, in a case where it is determined that the flow of the air at the predetermined flow velocity or higher in the direction from the first end portion 40a towards the connection portion 31 is not generated, the control section 5 proceeds to step S350, and determines that the mixture of the air in the liquid flowing in the circulation conduit 30 does not occur. Thus, the liquid feeding state detection process according to the present embodiment is ended.

Similarly as in the first embodiment, in the filter clogging detection process executed by the endoscope reprocessor 1 according to the present embodiment, the presence or absence of the mixture of the air from the atmospheric open conduit 40 in the liquid flowing in the circulation conduit 30 at the time of the running of the first pump 32 is detected, and the presence or absence of the occurrence of the clogging in the filter 61 is determined on the basis of the presence or absence of the mixture of the air.

According to the present embodiment, since the presence or absence of the mixture of the air in the liquid flowing in the circulation conduit 30 is not detected by using the absolute value of the flow rate or pressure in the circulation conduit 30 as the reference, the detection is not affected by the individual difference of the performance of the first pump 32 or the aging of the pump performance.

Therefore, in accordance with the endoscope reprocessor 1 according to the present embodiment and the control method for the endoscope reprocessor 1, the clogging occurrence in the filter 61 can be automatically accurately detected.

Note that the control section 5 serving as the control device includes a processor including a storage device such as a central processing unit (CPU), a ROM, or a RAM. For example, respective functions stored in the ROM are executed when various corresponding programs are read out by the CPU.

All or part of the functions of the processor may be configured by a logical circuit or an analog circuit, and processes of various programs may also be realized by an electronic circuit such as an FPGA.

The present invention is not limited to the above-described embodiments. Alterations can be made appropriately in a range without conflicting the gist or concept of the invention that is interpreted from the scope of the claims and the whole specification, and the control method for the endoscope reprocessor and the endoscope reprocessor accompanied by the above-mentioned alterations are also included in the technical scope of the present invention.

What is claimed is:

1. A control method for an endoscope reprocessor, wherein the endoscope reprocessor comprises:
   a treatment tank;
   a circulation conduit including a circulation opening opening in the treatment tank and a discharge opening opening in the treatment tank and linked to the circulation opening;
   a first pump configured to feed liquid from the circulation opening towards the discharge opening;
   an atmospheric open conduit including an atmosphere opening opening to an atmosphere and a connection opening connecting the atmosphere opening to the circulation conduit between the circulation opening and the discharge opening of the circulation conduit;
   a filter arranged in the treatment tank, the circulation opening, or between the circulation opening and the connection opening and configured to filter a liquid flowing from the treatment tank through the circulation opening into the circulation conduit; and
   a sensor arranged between the connection opening and the discharge opening of the circulation conduit, and configured to detect a liquid feeding state in the circulation conduit,
   wherein the control method comprises:
   measuring, by the sensor, a first flow rate of the circulation conduit during operation of the first pump in a state where the circulation conduit is open to the atmosphere via the atmosphere opening and the connection opening;
   measuring, by the sensor, a second flow rate of the circulation conduit in a state where the circulation conduit is not open to the atmosphere via the atmosphere opening and the connection opening;
   performing a comparison of the first flow rate and the second flow rate; and
   determining, based on a result of the comparison, presence or absence of mixture of air into the liquid flowing in the circulation conduit.

2. The control method according to claim 1,
   wherein the endoscope reprocessor further includes a reporting device, and
   wherein the control method further comprises driving the reporting device when the second flow rate is measured in a case where the mixture of air into the liquid flowing in the circulation conduit is detected at a time of the measurement of the first flow rate.

3. The control method according to claim 1,
   wherein the endoscope reprocessor further includes a signal transmission device configured to transmit a signal for driving a separate reporting device, and
   wherein the control method further comprises transmitting the signal for driving the reporting device when the presence of mixture of air into the liquid flowing in the circulation conduit is determined.

4. The control method according to claim 1,
   wherein the endoscope reprocessor further includes a second pump, arranged in the atmospheric open conduit, configured to feed liquid from the connection portion towards the end portion,
   wherein the measuring the first flow rate is operated during operation of the first pump in a state where the second pump is stopped, and
   wherein the measuring the second flow rate is operated during operation of the first pump.

5. The control method according to claim 1,
   wherein the determining is determining presence of mixture of air into the liquid flowing in the circulation conduit when the first flow rate is different from the second flow rate.

6. The control method according to claim 1, further comprising:
   before the measuring the second flow rate, switching the atmospheric open conduit to a closed state such that the circulation conduit is not open to the atmosphere via the atmosphere opening and the connection opening.

7. The control method according to claim 1, further comprising:
   before the measuring the first flow rate, switching the atmospheric open conduit to an open state such that the circulation conduit is open to the atmosphere via the atmosphere opening and the connection opening.

8. An endoscope reprocessor comprising:
   a treatment tank;
   a circulation conduit comprising a circulation opening opening in the treatment tank and a discharge opening opening in the treatment tank and linked to the circulation opening;
   a first pump configured to feed liquid from the circulation opening towards the discharge opening;
   an atmospheric open conduit comprising an atmosphere opening opening to an atmosphere and a connection opening connecting the atmosphere opening to the circulation conduit between the circulation opening and the discharge opening of the circulation conduit;
   a filter arranged in the treatment tank, the circulation opening, or between the circulation opening and the connection opening and configured to filter a liquid flowing from the treatment tank through the circulation opening into the circulation conduit;
   a sensor arranged between the connection opening and the discharge opening of the circulation conduit, and configured to detect a liquid feeding state in the circulation conduit; and
   a controller configured to:
   control the sensor to measure a first flow rate of the circulation conduit during operation of the first pump in a state where the circulation conduit is open to the atmosphere via the atmosphere opening and the connection opening;

control the sensor to measure a second flow rate of the circulation conduit in a state where the circulation conduit is not open to the atmosphere via the atmosphere opening and the connection opening;

perform a comparison of the first flow rate and the second flow rate; and determine, based on a result of the comparison, presence or absence of mixture of air into the liquid flowing in the circulation conduit.

9. The endoscope reprocessor according to claim 8, further comprising:

a reporting device connected to the control device, wherein the controller is configured to drive the reporting device when the second flow rate is measured in a case where the mixture of air into the liquid flowing in the circulation conduit is detected at a time of the measurement of the first flow rate.

10. The endoscope reprocessor according to claim 8, further comprising:

a signal transmission device configured to transmit a signal for driving a separate reporting device, wherein the controller is configured to transmit a signal for driving the reporting device when the presence of the mixture of air into the liquid flowing in the circulation conduit is determined.

11. The endoscope reprocessor according to claim 8, wherein the atmospheric open conduit has a flow resistance higher than a flow resistance of the circulation conduit.

12. The endoscope reprocessor according to claim 8, further comprising:

a second pump, arranged in the atmospheric open conduit, configured to feed liquid from the connection portion towards the end portion, wherein the controller is configured to:

control the sensor to measure the first flow rate during operation of the first pump in a state where the second pump is stopped; and control the sensor to measure the second flow rate during operation of the first pump.

13. The endoscope reprocessor according to claim 8, wherein the controller is configured to determine presence of mixture of air into the liquid flowing in the circulation conduit when the first flow rate is different from the second flow rate.

14. The endoscope reprocessor according to claim 8, wherein the controller is configured to, before the measuring the second flow rate, switch the atmospheric open conduit to a closed state such that the circulation conduit is not open to the atmosphere via the atmosphere opening and the connection opening.

15. The endoscope reprocessor according to claim 8, wherein the controller is configured to, before the measuring the first flow rate, switch the atmospheric open conduit to an open state such that the circulation conduit is open to the atmosphere via the atmosphere opening and the connection opening.

16. An apparatus for controlling an endoscope reprocessor, wherein the endoscope reprocessor comprises:

a treatment tank;

a circulation conduit including a circulation opening opening in the treatment tank and a discharge opening opening in the treatment tank and linked to the circulation opening;

a first pump configured to feed liquid from the circulation opening towards the discharge opening;

an atmospheric open conduit including an atmosphere opening opening to an atmosphere and a connection opening connecting the atmosphere opening to the circulation conduit between the circulation opening and the discharge opening of the circulation conduit;

a filter arranged in the treatment tank, the circulation opening, or between the circulation opening and the connection opening and configured to filter a liquid flowing from the treatment tank through the circulation opening into the circulation conduit; and a sensor arranged between the connection opening and the discharge opening of the circulation conduit, and configured to detect a liquid feeding state in the circulation conduit, and wherein the apparatus comprises one or more processors configured to:

control the sensor to measure a first flow rate of the circulation conduit by the sensor during operation of the first pump in a state where the circulation conduit is open to the atmosphere via the atmosphere opening and the connection opening;

control the sensor to measure a second flow rate of the circulation conduit in a state where the circulation conduit is not open to the atmosphere via the atmosphere opening and the connection opening;

perform a comparison of the first flow rate and the second flow rate; and determine, based on a result of the comparison, presence or absence of mixture of air into the liquid flowing in the circulation conduit.

* * * * *